(12) United States Patent
Gann et al.

(10) Patent No.: US 7,320,673 B2
(45) Date of Patent: Jan. 22, 2008

(54) TAMPON APPLICATOR HAVING A RUPTURABLE MEMBRANOUS CAP

(75) Inventors: Diana Lynne Gann, Lebanon, OH (US); Thomas Ward Osborn, III, Clifton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 162 days.

(21) Appl. No.: 10/791,976

(22) Filed: Mar. 3, 2004

(65) Prior Publication Data

US 2005/0197616 A1 Sep. 8, 2005

(51) Int. Cl.
*A61F 13/30* (2006.01)
*A61F 13/28* (2006.01)
*A61F 13/32* (2006.01)

(52) U.S. Cl. ............. 604/14; 604/12; 604/15; 604/385.18; 604/904

(58) Field of Classification Search ......... 604/11–18, 604/904, 385.17, 385.18
See application file for complete search history.

(56) References Cited

U.S. PATENT DOCUMENTS

| | | | |
|---|---|---|---|
| 1,969,671 A | 8/1934 | Nelson | |
| 2,351,836 A * | 6/1944 | Popper | 604/16 |
| 3,674,025 A | 7/1972 | Bleuer | |
| 3,706,311 A | 12/1972 | Kokx | |
| 3,760,808 A | 9/1973 | Bleuer | |
| 4,312,348 A | 1/1982 | Friese | |
| 4,479,791 A | 10/1984 | Sprague | |
| 4,592,740 A | 6/1986 | Mahruki | |
| 5,569,177 A | 10/1996 | Fox | |
| 5,693,009 A | 12/1997 | Fox | |
| 5,766,145 A | 6/1998 | Fox | |
| 5,817,047 A | 10/1998 | Osborn | |
| 5,928,183 A | 7/1999 | Fox | |
| 5,988,386 A | 11/1999 | Morrow | |
| 6,024,716 A | 2/2000 | Rejai | |
| 6,056,714 A | 5/2000 | McNelis | |
| 6,095,998 A | 8/2000 | Osborn | |
| 6,254,566 B1 | 7/2001 | Buck | |
| 6,302,862 B1 | 10/2001 | Osborn | |
| 2003/0028138 A1 | 2/2003 | Karapasha et al. | |
| 2003/0028177 A1 | 2/2003 | Berg, Jr. et al. | |

* cited by examiner

*Primary Examiner*—Karin Reichle
(74) *Attorney, Agent, or Firm*—James E. Oehlenschlager; Ingrid N. Hackett; David M. Weirich

(57) ABSTRACT

A feminine hygiene product which has a tampon and a tampon applicator. The tampon applicator has a rupturable membranous cap permanently associated with a tampon holder tube. The tampon holder tube has a hollow interior portion, an interior surface, an exterior surface, an outer perimeter, a longitudinal axis, a first end dimensioned for insertion into a vaginal cavity, and a second end positioned oppositely to the first end. The tampon is housed in the tampon holder tube within the hollow interior portion of the tampon holder tube and is substantially aligned with the longitudinal axis of the tampon holder tube in a pre-expelled position. The rupturable membranous cap covers at least a portion of the tampon. During expulsion of the tampon from the tampon holder tube, the rupturable membranous cap reorients the tampon into a direction substantially non-aligned to the longitudinal axis of the tampon holder tube.

9 Claims, 6 Drawing Sheets

TAMPON APPLICATOR HAVING A RUPTURABLE MEMBRANOUS CAP

FIELD OF THE INVENTION

The present invention relates to a novel tampon applicator having a rupturable membranous cap positioned over the tampon.

BACKGROUND OF THE INVENTION

It is known that the internal vaginal cavity in its normal collapsed state has a much wider dimension in its transverse plane than in its vertical plane. It is also well known that the minimum dimension of the vagina is near the introitus while the maximum dimension is near the cervix. It is desirable, therefore, when considering a tampon for catamenial use, to provide a structure which, in its initial state, is of a size small enough to pass through the vaginal orifice without discomfort, and once inside the vaginal cavity and beyond the restrictions of the orifice, can expand, particularly in the lateral direction, to cover substantially large portions of the vaginal surface from one side to the other to prevent early bypass of the menstrual discharges from the cervix. This side-to-side coverage is a preferred object of this invention. Further, since the vaginal wall in its normal collapsed state is flaccid and has multiple folds and wrinkles which provide channels through which a significant portion of the menstrual fluids normally flow, it is also important that the absorbent tampon be as soft and conformable as possible to conform to the shape of the vaginal cavity and fit within these channels to minimize leakage.

Generally, absorbent catamenial tampons are small, highly compressed, cylindrical plugs of about ⅜ to about ½ inch (about 1.0 cm to about 1.3 cm) in diameter and from about 1½ to about 2½ inches in length (about 3.8 cm to about 6.4 cm). Because of the need for absorbent capacity, they are usually formed from batts much larger in size than the vaginal orifice and compressed to the small size indicated above to facilitate insertion. As fluid is absorbed, these compressed tampons are designed to re-expand. While it has been found that these compressed tampons perform their intended function tolerably well, even the best of them do not re-expand sufficiently, or fast enough, to provide good transverse coverage against leakage even though the vertical blockage may be satisfactory. Further, most of these tampons often use only a small portion of their absorptive capacity before leakage. Since these tampons rely on some fluid absorption to re-expand, it is clear that fluid bypass and leakage can occur prematurely, particularly immediately or soon after the time of insertion.

Fortunately, it has been found during development of the present invention that a tampon inserted into the vaginal cavity using the tampon applicator constructed according to the present can provide even further improvements in comfort, low wearing awareness, and performance as compared to currently marketed tampon applicators and previous attempts to improve tampon applicators.

SUMMARY OF THE INVENTION

The present invention encompasses a feminine hygiene product. The feminine hygiene product comprises a tampon and a tampon applicator. The tampon comprises an outer tampon perimeter, an insertion end, and a withdrawal end opposed to the insertion end. The insertion end has a top portion. The tampon applicator comprises a rupturable membranous cap permanently associated with a tampon holder tube at its insertion end. The tampon holder tube has a hollow interior portion, an interior surface, an exterior surface, an outer perimeter, a longitudinal axis, a first end dimensioned for insertion into the vaginal cavity, and a second end positioned oppositely to the first end. The tampon is housed in the tampon holder tube within the hollow interior portion of the tampon holder tube and is substantially aligned with the longitudinal axis of the tampon holder tube in a pre-expelled position. The rupturable membranous cap covers at least a portion of the insertion end of the tampon. During expulsion of the tampon from the tampon holder tube, the tampon contacts the rupturable membranous cap and the rupturable membranous cap reorients the tampon into a direction substantially non-aligned to the longitudinal axis of the tampon holder tube.

In one embodiment, the tampon comprises a fluid permeable bag and absorbent material loosely dispersed within the fluid permeable bag. Additionally, the tampon can rotate during expulsion from the applicator. Optionally, at least a portion of the tampon and at least a portion of the rupturable membranous cap may rotate together during expulsion.

The tampon and applicator can also comprise a plunger being slidably mounted in the hollow interior portion of the tampon holder tube. The plunger is adapted to expel the tampon through the first end of the tampon holder tube.

Before expulsion of the tampon, the feminine hygiene product can further comprise a region of rupture on the rupturable membranous cap and a tampon holder tube region of rupture on the tampon holder tube. The region of rupture and the tampon holder tube region of rupture may be in contact with one another before expulsion of the tampon. The region of rupture on the rupturable membranous cap and the tampon holder tube region of rupture on the tampon holder tube can have a configuration selected from a group consisting of C-shaped, conical, diagonal, arched, parabolic, round, and semi-spherical. The region of rupture on the rupturable membranous cap and the tampon holder tube region of rupture on the tampon holder tube may comprise perforations.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

FIG. 1b is a top view of the feminine hygiene product of FIG. 1a.

DETAILED DESCRIPTION OF THE INVENTION

Figure 1A:
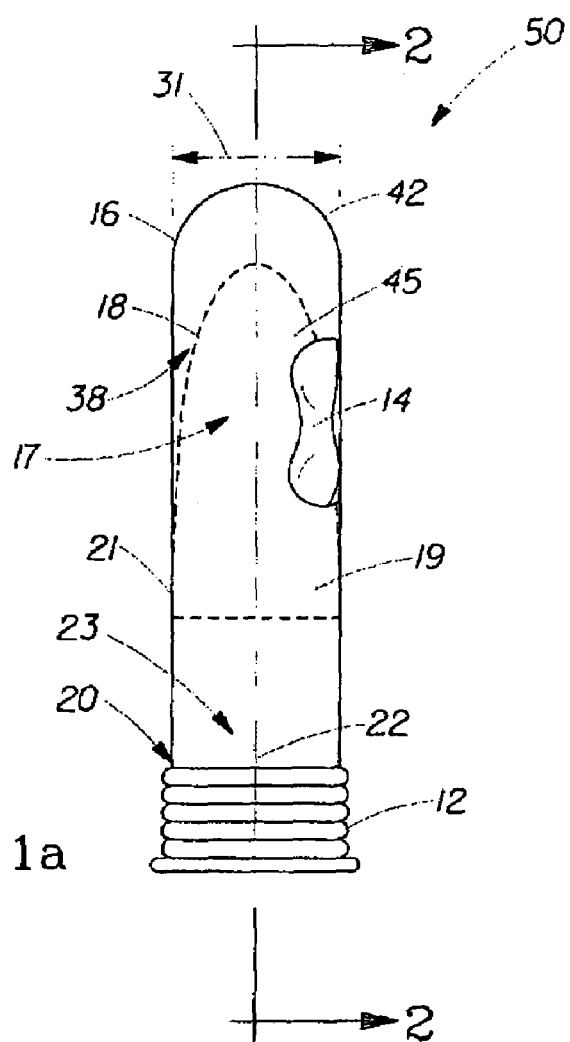
FIG. 1a is a side view of a feminine hygiene product with a cut out section showing the tampon in its pre-expelled state.

The following are terms which will assist the reader in best understanding the features of the invention, but do not introduce limitations in the terms inconsistent with the context in which they are used in this specification. These definitions are not intended to be limiting.

As used herein, the term "feminine hygiene product" 50 comprises a tampon 14, a rupturable membranous cap 16, and a tampon holder tube 19. The tampon 14 or at least a part thereof is typically present in the tampon holder tube 19, which is typically hollow, and is able to hold a tampon 14 such that a part of the tampon 14 or the entire tampon 14 is in the interior (or inside) of the tampon holder tube 19. Thus, the tampon 14 or a part thereof is covered or enclosed by the tampon holder tube 19.

As used herein, "tampon holder tube" 19 refers to an article that facilitates the insertion of a tampon 14 into the vagina of the wearer. The tampon holder tube 19 has at least a portion which is permanently connected to the rupturable membranous cap 16 during expulsion. The tampon holder tube 19 has a first end 17 and a second end 23 opposite the first end 17. The first end 17 is the portion of the tampon holder tube 19 in which the tampon 14 is expelled. The second end 23 is the portion of the tampon holder tube 19 in which the axial force 24 is applied to expel the tampon 14. The tampon holder tube 19 may comprise one or more units. Any known hygienically designed tampon holder tube 19 may be used for insertion of a tampon 14, including the so-called telescoping, tampon holder tube 19 and plunger 13.

As used herein, the term "rupturable membranous cap" 16 refers to a covering which is preset over or on at least a portion of the tampon 14. The rupturable membranous cap 16 has a top 42 and a bottom 38. As the tampon 14 is expelled, it bursts the membrane, leaving a connection (i.e., the hinge 39) between the rupturable membranous cap 16 and the tampon holder tube 19. The hinge 39 allows the rupturable membranous cap 16 to rotate during expulsion of the tampon 14 from the tampon holder tube 19. It is desirable for one portion of the bottom 38 to contain regions of rupture 18 and the other portion of the bottom 38 of the rupturable membranous cap 16 to be connected to the tampon holder tube 19 in such a way as to result in a hinge 39.

As used herein, the term "hinge" 39 refers to a portion of the rupturable membranous cap 16 which does not have any regions of rupture 18 and is located at the bottom 38 of the rupturable membranous cap 16. The hinge 39 allows the rupturable membranous cap 16 to remain flexibly and fixedly attached to the tampon holder tube 19. Moreover, the hinge 39 could be extensible and stretchable.

The term "regions of rupture" 18 refers to the feminine hygiene product 50 comprising regions of perforations or regions of varied thickness. The regions of rupture 18 on the feminine hygiene product 50 are located between the rupturable membranous cap 16 and the tampon holder tube 19. The regions of rupture 18 are thinner compared to other regions of the rupturable membranous cap 16 and/or tampon holder tube 19 to facilitate the rupture.

As used herein, the term "rupture" refers to the bursting, tearing, or breaking of regions of rupture 18 which allow the tampon 14 to expel from the tampon holder tube 19.

The term "joined" or "attached" encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element; i.e., one element is essentially part of the other element.

As used herein, the term "tampon" 14 refers to any type of absorbent structure that is inserted into the vaginal canal or other body cavities for the absorption of fluid there from, or for the delivery of active materials, such as medicaments, or moisture.

By the terms "directionally expel", "directed expulsion," or "directional expulsion" it is meant herein that embodiments of the feminine hygiene product 50 of the present invention that will expel along the longitudinal axis 22 of the tampon holder 10 before reorientation of the tampon 14 by the rupturable membranous cap 16.

Figure 4:
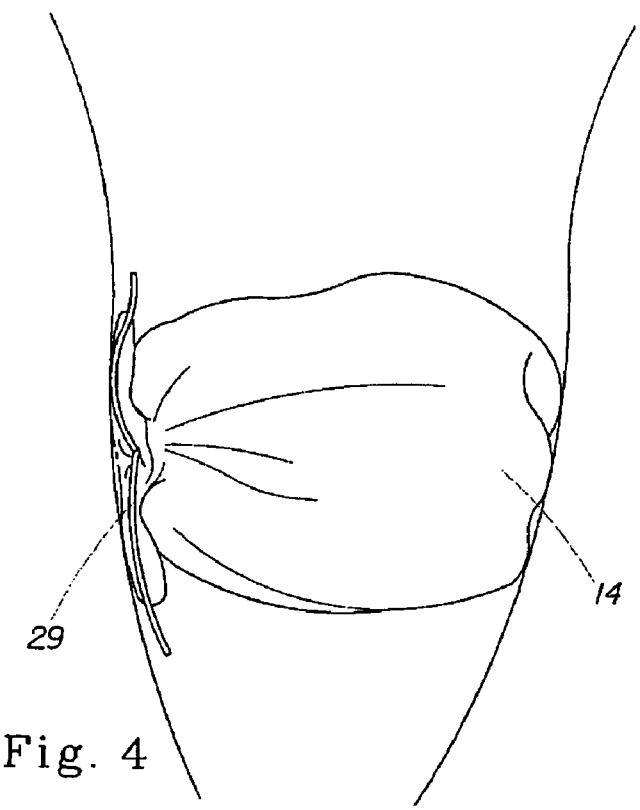
FIG. 4 is a plan view of a tampon fitting within the vaginal cavity of a female user after the tampon has been expelled by the applicator of the present invention.

By the term "side-to-side coverage," it is meant herein that the tampon 14, once expelled, will have at least two sections thereof positioned outwardly toward the sides or walls of a female user's vaginal cavity (FIG. 4).

By the term "pre-expelled position," it is meant herein a position in which the tampon 14 is placed or packed into the tampon holder tube 19 positioned for the tampon's successful expulsion through the tampon holder tube 19.

The term "expelled," as used herein, is meant the position after the tampon 14 is forced out of the feminine hygiene product 50 (FIG. 4).

Figure 3:
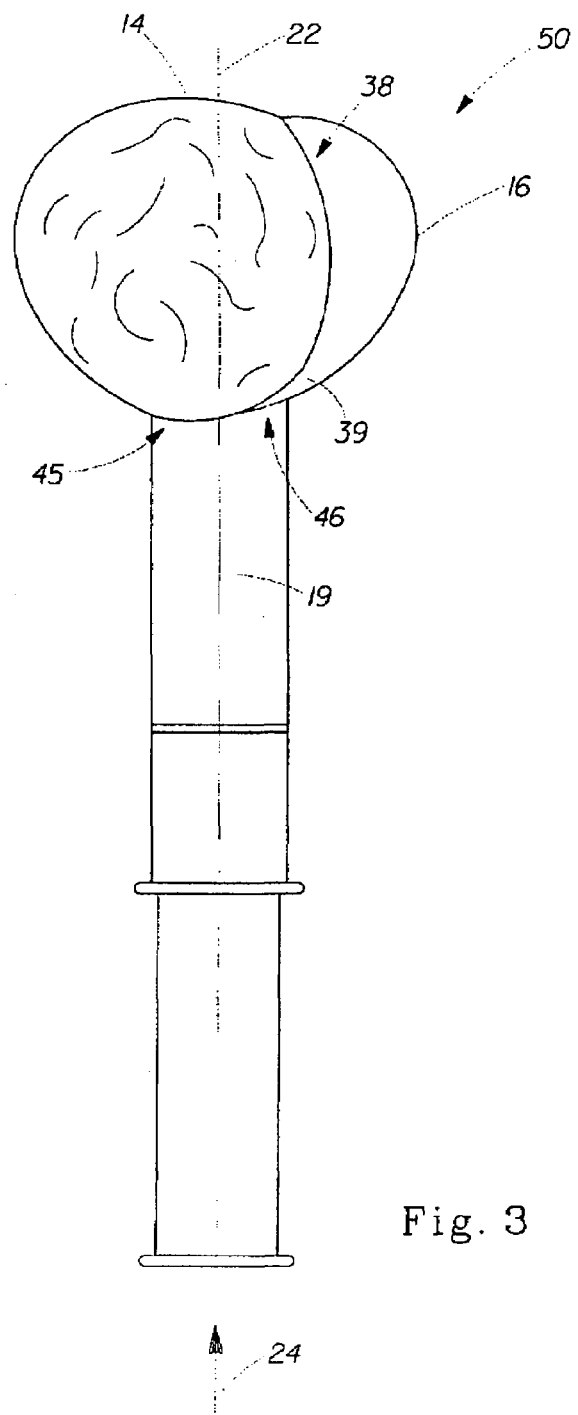
FIG. 3 is a side view of the feminine hygiene product in its partially-expelled state.

The term "axial force" 24, as used herein, is meant the force 24 applied along the longitudinal axis 22 in the direction of expelling the tampon 14 from the feminine hygiene product 50 (FIG. 3).

As used herein, "cm" is centimeter, "gsm" is grams per square meter, "mm" is millimeters, "ml" is milliliters, and "sec" is seconds.

The following is a description of typical arrangements of the invention, referring to the Figures. Referring to FIG. 1a, the present invention relates to reorienting a tampon 14 into a direction substantially non-aligned to the longitudinal axis 22 of a tampon holder tube 19 during expulsion of the tampon 14 from the tampon holder tube 19. The feminine hygiene product 50 includes a rupturable membranous cap 16 and a tampon holder tube 19. The rupturable membranous cap 16 has a top 42, a first bottom portion 38, and a second bottom portion 40 containing a hinge 39 (shown in FIG. 2). The first bottom portion of the rupturable membranous cap 16 is adjacent to regions of rupture 18. The second bottom portion 40 (shown in FIG. 2) of the rupturable membranous cap 16 is adjacent to the tampon holder tube 19.

The tampon holder tube 19 has a first end 17, a second end 23 opposite to the first end 17, and a finger grip 12. The first end 17 has a first top portion 45 and a second top portion 46 (shown in FIG. 2). The first top portion 45 may be adjacent to the regions of rupture 18. The second top portion 46 (shown in FIG. 2) may be adjacent to the hinge 39 (shown in FIG. 2).

The feminine hygiene product 50 has a pre-expelled state, a partially expelled state, and an expelled state. During the pre-expelled state, as is readily seen in FIG. 1a, the tampon 14 sits within the tampon holder tube 19 and is substantially aligned with the tampon holder tube 19. The tampon 14 can remain snugly therein without any outside force to sustain its position in the tampon holder tube 19. A portion of the feminine hygiene product 50 comprises a tampon holder tube 19 having a hollow interior portion (not denoted), an interior surface (not denoted), an outer perimeter 20, an exterior surface 21, longitudinal axis 22, a first end 17, a second end 23 positioned oppositely to the first end 17, a first top portion 45, a second top portion 46 which is adjacent to the first top portion 45, and a finger grip 12.

Another portion of the feminine hygiene product 50 comprises a rupturable membranous cap 16 comprising a top of the cap 42, a bottom of the cap 38, a top portion of the expulsion end 31, and a hinge 39. Regions of rupture 18 are capable of separating a portion of the rupturable membranous cap 16 and the tampon holder tube 19 when the regions of rupture 18 rupture.

Figure 1B:
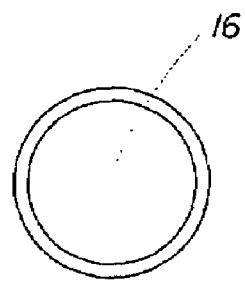

FIG. 1b shows the top view of the product from adjacent rupturable membranous cap 16.

Figure 2:
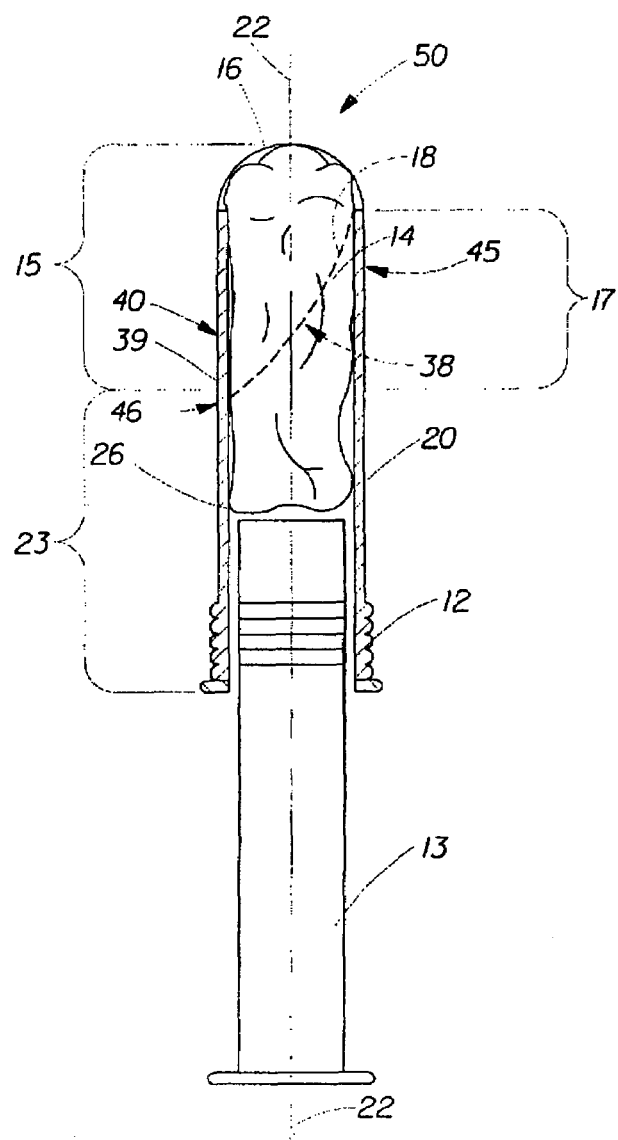
FIG. 2 is a cross-section view of the tampon holder tube along a line 2-2 of FIG. 1a in combination with a plunger.

Referring to FIG. 2, tampon holder tube 19 has a first end 17 and a second end 23 which is opposite to the first end 17. Before expulsion of the tampon 14 from the tampon holder tube 19, the tampon 14 is in a vertical position. During expulsion of the tampon 14 from the tampon holder tube 19 into the vaginal cavity, the tampon 14 changes its orientation to a position that is substantially non-aligned to the tampon holder tube's 19 pre-expelled vertical position. As a result, the tampon's 14 position during insertion is in a different position from the tampon's 14 position after insertion into the vaginal cavity.

FIG. 2 shows a tampon holder tube 19 containing a tampon 14. The tampon 14 has a top portion 15 that partially extends from the tampon holder tube 19 into the rupturable membranous cap 16. In other words, the rupturable membranous cap 16 substantially covers the top portion 15 of the tampon 14 and the withdrawal end 26 of the tampon 14 is enclosed in the tampon holder tube 19. In an alternative embodiment, the rupturable membranous cap 16 may be in contact with the entire tampon top portion 15. The bottom 38 of the rupturable membranous cap 16 and the first top portion 45 of the tampon holder tube 19 can be separated by regions of rupture 18.

Also, as seen in FIG. 2, alternatively, the feminine hygiene product 50 may include a plunger 13 that is telescopically and slidably mounted in the tampon holder tube 19 distal to the first end 17 and adapted to expel the tampon 14 from the tampon holder tube 19. However, such user-activated expulsion may occur either by a plunger 13, plunger-like device, or digitally with a user's finger(s).

Referring to FIG. 2, to use the feminine hygiene product 50 of the present invention the user will typically hold the tampon holder tube 19 in one hand at the finger grip 12 on the same. When the plunger 13 is present, the user holds the end of the plunger 13, such as with her thumb and middle finger, and pushes the plunger 13 inwardly to slide the plunger 13 within the tampon holder tube 19. In practice, a user pushes the inserted plunger 13 until the entire tampon 14 is deployed from the feminine hygiene product 50. The user then pulls the tampon holder tube 19 (i.e., with the plunger 13 inside) out of the user's vaginal opening.

In the partially expelled state, as is readily seen in FIG. 3, the tampon 14 is shown being expelled with an axial force 24 from feminine hygiene product 50. When the tampon 14 is pushed out of the tampon holder tube 19 with an axial force 24 applied from the bottom and simultaneously pushed toward the first end 17 along the longitudinal axis 22 of the tampon holder tube 19. The bottom 38 of the rupturable membranous cap 16 may separate from the first top portion 45 which is adjacent to the regions of rupture 18 when the regions of rupture 18 rupture. Additionally, the rupturable membranous cap 16 may extend before the regions of rupture 18 are ruptured. During expulsion, the tampon 14 can be joined to the rupturable membranous cap 16. The rupturable membranous cap 16, specifically the hinge 39, aids the tampon 14 to change from its first position (FIG. 1a) in its pre-expelled state to its second position (FIG. 3) in its partially expelled feminine hygiene product 50 state and finally to a third position in its fully expelled feminine hygiene product 50 state (FIG. 4).

In one non-limiting example, in its expelled state, as shown in FIG. 4, the tampon 14 in the case of a bag tampon is positioned in the vaginal cavity of a female user so that improved side-to-side coverage of the vaginal opening is achieved where a trailing edge 29 of the tampon 14 fits within the vaginal cavity. Contact of a female user's vaginal walls is a highly desired characteristic of a tampon 14 when it is worn during a female's menstruation period. Menses, whether highly viscous or less viscous, when flowing out of the user, follows the geometry of a female user's vaginal walls. In other words, menses may substantially flow along the vaginal walls of a female user. FIG. 4 shows how such side-to-side coverage in the vaginal cavity is expected to occur when using the present feminine hygiene product 50.

Figure 5:
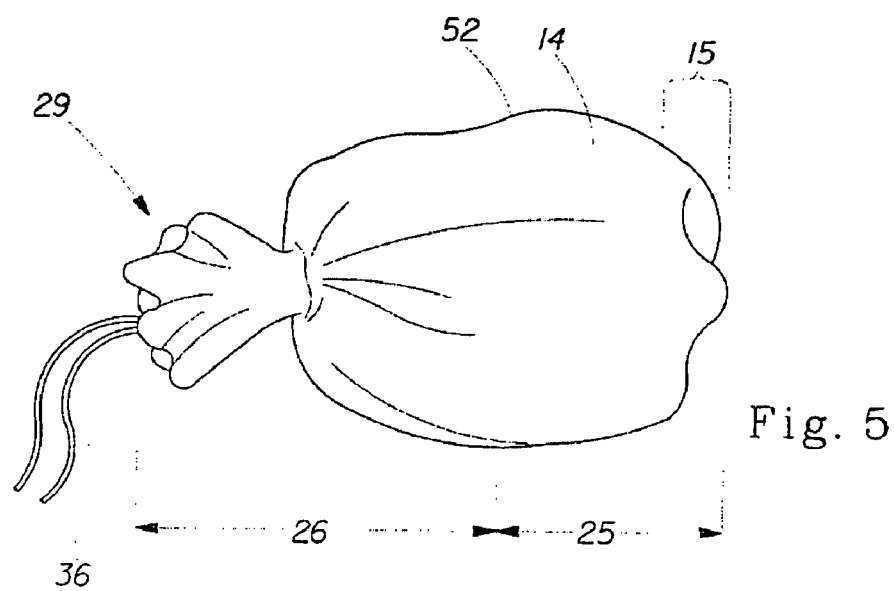
FIG. 5 is a plan view of the tampon.

FIG. 5 is a plan view of a tampon 14. The tampon 14 has a withdrawal end 26 opposed to an insertion end 25 having a top portion 15, an outer tampon perimeter 52, the trailing edge 29, and a withdrawal string 36. A key advantage of the feminine hygiene product 50 (shown in FIG. 1a) discussed herein is that the tampon 14 can be inserted into the feminine hygiene product 50 (shown in FIG. 1a) in any orientation and/or folded in any manner (i.e., concave or convex) and, once expelled into the vaginal cavity, still provide effective side-to-side coverage in the vaginal cavity. In one non-limiting example, if the tampon 14, as shown in FIG. 5, is placed with the withdrawal end 26 of the tampon 14 inserted first into the second end 23 of the tampon holder tube 19 (FIG. 1a), the tampon 14 will expel and still provide side-to-side coverage in the vaginal cavity.

Figure 6:
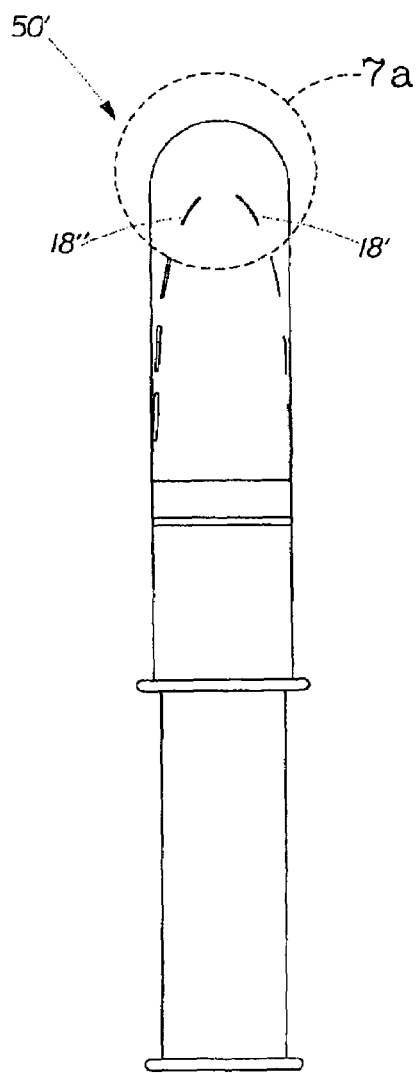
FIG. 6 is a side view of an alternative embodiment of the feminine hygiene product.
Figure 7A:
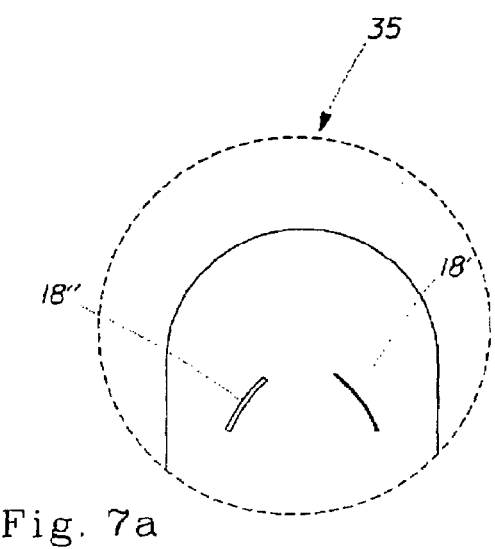
FIG. 7a is an enlarged partial view of FIG. 6.
Figure 7B:
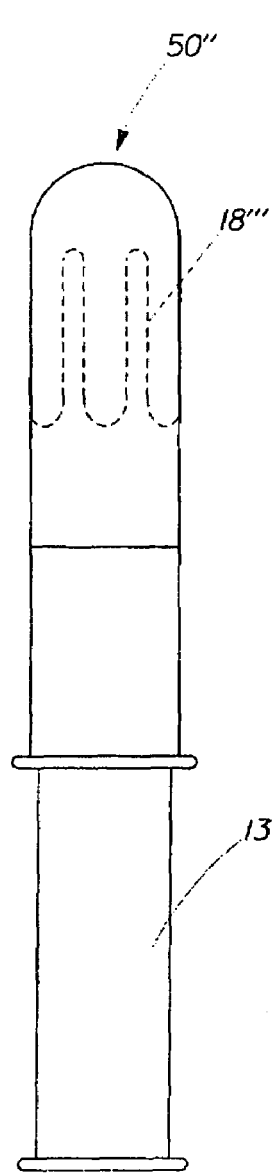
FIG. 7b is an alternative embodiment of a feminine hygiene product in its pre-expelled state.
Figure 7C:
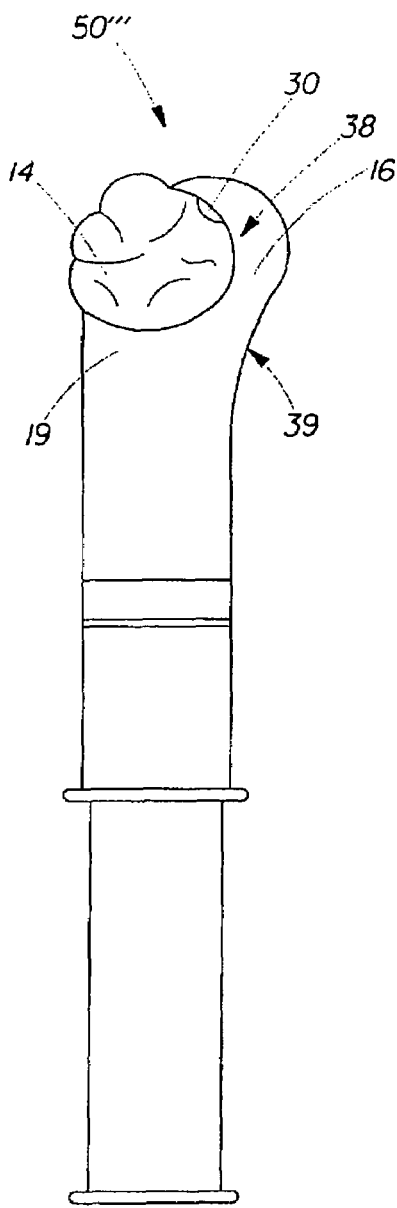
FIG. 7c is an alternative embodiment of a feminine hygiene product in its partially-expelled state.

FIG. 6 is an alternative embodiment of a feminine hygiene product 50'. The regions of rupture 18',18" are shown. FIG. 7a is a partial view 35 of FIG. 6 showing the regions of rupture 18',18', 18". FIG. 7b is an alternative embodiment of a feminine hygiene product 50'''. The regions of rupture 18''' are shown. Also, the plunger 13 is shown. FIG. 7c shows an alternative embodiment of feminine hygiene product 50''' partially-expelling tampon 14. A portion of the feminine hygiene product 50''' comprises a rupturable membranous cap 16 comprising a projection 30 and a hinge 39. The regions of rupture 18 allowed a portion of the rupturable membranous cap 16 and a portion of the tampon holder tube 19 to separate.

Below will detail each component of the feminine hygiene product 50.

I. Rupturable Membranous Cap

Referring to FIG. 1a, generally, the rupturable membranous cap 16 helps to change the orientation of the tampon 14 as it passes through the tampon holder tube 19 along the longitudinal axis 22. The rupturable membranous cap 16 has a top 42, a bottom 38, and the hinge 39 (FIG. 2). As shown in FIG. 3, the bottom 38 of the rupturable membranous cap 16 is adjacent to the regions of rupture 18 and the tampon holder tube 19. As also shown in FIG. 3, the hinge 39 is adjacent to the tampon holder tube 19.

As shown in FIG. 2, before expulsion of the tampon 14 from the tampon holder tube 19, the rupturable membranous cap 16 is disposed over at least a portion of the first end of the tampon 14. During the pre-expulsion state and the expulsion state, at least a portion of the tampon 14 is joined to the rupturable membranous cap 16. In one non-limiting example, during the pre-expulsion state, the rupturable membranous cap 16 is not directly adjacent to the tampon 14 because a lubricant is placed onto either the rupturable membranous cap 16 and/or the tampon 14. A lubricant can be used to increase the comfort during insertion of the tampon 14 into the vaginal cavity.

Referring to FIG. 1a, the bottom portion 38 of the rupturable membranous cap 16 comprises two regions. The first region of the bottom portion 38 is adjacent to the regions of rupture 18. The second region of the bottom 38 portion contains the hinge 39 and is adjacent to the tampon holder tube 19. The regions of rupture 18 are located on a substantial portion of the outer perimeter 20 of the rupturable membranous cap 38. Thus, upon expulsion of the tampon 14 from the tampon holder tube 19, the pattern for the regions of rupture 18 can result in the bottom 38 of the second region of the rupturable membranous cap 16 remaining attached to the tampon holder tube 19 by the hinge 39 contained in the rupturable membranous cap 16. In other words, the hinge 39 is located in the region(s) where there are not regions of rupture 18.

Referring to FIG. 2, the rupturable membranous cap 16 may be placed in any location adjacent to the first end 17 of the tampon holder tube 19 and at any distance to the tampon 14 so long as the rupturable membranous cap 16 may remain joined to the tampon 14 during expulsion to help change the orientation of the tampon 14 as it passes through the tampon holder tube 19 along the longitudinal axis 22. In one embodiment, as seen in FIG. 2, a portion of the rupturable membranous cap 16 is placed over the top 15 of the tampon 14. The rupturable membranous cap 16 may be in close proximity with the tampon 14. In many embodiments, the rupturable membranous cap 16 can be in contact with the tampon 14 so that the distance between the entire rupturable membranous cap 16 and the tampon 14 is zero.

It is further noted herein that the shape, size, or configuration of the rupturable membranous cap 16 may vary as long as the rupturable membranous cap 16 remains joined to the tampon 14 and reorients the tampon 14 during expulsion of the tampon 14. The rupturable membranous cap 16 is in no way limited by the size or shape that it may assume except that it should not hinder the expulsion of the tampon 14. One of skill in the art will readily recognize obvious variants on those presented in the patent application herein. One versed in the art can imagine that the shape of the rupturable membranous cap 16 might be circular, square, rectangular, triangular, arced, curved, or any other conceivable shape possible as long as any such shape would work effectively to fully and properly aid in joining the tampon 14 to the rupturable membranous cap 16 and reorienting the tampon 14.

As shown in FIG. 1b, the top view of the rupturable membranous cap 16 forms a substantially closed end configuration at the top of the feminine hygiene product 50. This rounded shape is useful to facilitate insertion of the applicator into the vaginal cavity.

The rupturable membranous cap 16 may also be reinforced by any known ways in the art. The rupturable membranous cap 16 can be reinforced by varying film thickness, added thickness of film, overlapping sealed films, and/or any other reinforcement means known in the art.

Referring to FIG. 3, the rupturable membranous cap 16 comprises a hinge 39. The hinge 39 is located at the bottom 38 of the rupturable membranous cap 16. The hinge 39 fixedly attaches the rupturable membranous cap 16 and the tampon holder tube 19. In other words, the hinge 39 is located adjacent to the second top portion 46 of the tampon holder tube 19. The hinge 39 does not contain any regions of rupture 18. During expulsion, after the regions of rupture 18 are ruptured, the hinge 39 aids the rupturable membranous cap 16 to remain fixedly and flexibly joined to the tampon holder tube 19. The hinge 39 also aids in the reorientation of the tampon 14. Thus, the hinge 39 of the rupturable membranous cap 16 is a flexible part of the rupturable membranous cap 16 permanently associated with the tampon holder tube 19. Moreover, the hinge 39 could be extensible. In one non-limiting example, the hinge 39 could be moving parts which connect the rupturable membranous cap 16 and the tampon holder tube 19.

It is further noted herein that the shape or configuration of the hinge 39 may vary as long as the hinge 39 is permanently connected to the tampon holder tube 19. Specifically, the hinge 39 must remain connected to the tampon holder tube 19 during the pre-expulsion, expulsion, and post-expulsion of the tampon 14. The hinge 39 is in no way limited by the size or shape that it may assume except that it should not hinder directional expulsion of a tampon 14 and the hinge 39 should remain flexible enough to allow the tampon 14 to expel. One of skill in the art will readily recognize obvious variants on those presented in the patent application herein. One versed in the art can imagine that the hinge 39 might be circular, square, rectangular, triangular, arcs, curves, or any other conceivable shape possible as long as any such shape would work effectively to fully and properly provide flexibility and is capable of joining the rupturable membranous cap 16 and the tampon holder tube 19. In one embodiment, the hinge 39 has regions of rupture 18 on both sides of the hinge 39.

a. Material of the Rupturable Membranous Cap

While not wishing to be bound by any particular theory, the rupturable membranous cap 16 may be made from made from polyethylene; duraform polyamide; plastic; paper; cardboard; degradable, compostable thermoplastic materials, typically water dispersible or water soluble materials; biodegradable materials; and other materials known in the art. For example, the rupturable membranous cap 16 can be constructed of a spiral-wound paperboard construction and coated on the exterior with a coating material, such as wax. Applicators may be flushable through the toilet or discarded in the trash. The rupturable membranous cap 16 may also be made of any type of planar, flexible film, or other deformable substrate. The typical film material used to make a rupturable membranous cap 16 may be a smooth or embossed sheet-shaped substrate.

Film materials may be a single layer or a planar laminate or may be comprised of connected structures of two or more film materials joined to each other in a horizontal side-by-side arrangement, for example lap or edge-to-edge butt joints to form the film. Such joined materials may leave a weld or seam, though care should be taken to minimize the length, width, and height of such welds.

Films may be made of one or more of the following substrates and resins: polyolefins; cellulose materials and derivatives, including cellulose ethers, ethyl, and methyl celluloses; cellulose esters, including cellulose acetates, formates, vinyl polymer derivatives, or more typically cellophane and/or polyethylenes; polypropylenes; latex; nylon; polyesters; and polystyrenes. Some other resins and films include polylactides, polyester amides, aliphatic esters, aliphatic-aromatic copolyesters, polyhydroxyalkanoates, polyalkylene succinate, polyvinyl alcohols, cellulosic polymers, starch-based materials, and/or polycaprolactone. Polyolefin, such as polyethylenes and polypropylenes and/or biodegradable films are typical. Polyolefins are also discussed and defined in "*Plastics and Films*", chapter 2, by J. H. Briston, $3^e$ edition, published in 1988, Langman Scientific & Technical.

The rupturable membranous cap 16 may be porous, micro-porous, or non-porous. The rupturable membranous cap 16 may be gas and/or water permeable. The rupturable membranous cap 16 may be hydrophobic or hydrophilic; thermoplastic; thermosetting, water soluble; water-disintegratable; or water-dispersible. The rupturable membranous cap 16 may shrink upon exposure to heat or application of pressure or vacuum. Some films that exhibit these qualities are single or biaxially oriented films, such as polypropylenes.

The film used to make the rupturable membranous cap 16 may be made by any process known in the art including casting, extrusion, or blown extrusion processes. The rupturable membranous cap 16 may have a functional coating on one or each surface that may change the film's properties such as hydrophilicity, hydrophobicity, coefficient of friction, heat sealing properties, gas, water permeability, colour, tactile feel, and/or odour.

The film may be a highly extensible film. A highly extensible film has an elongation at break in the machine direction of at least 150%, typically from 200% to 1000%, or from 350% to 850%. Typically, the elongation at break in the cross-machine direction is in the same range as mentioned above. An example of a typical material is polyethylene DH215, available from Clopay, which has an elongation at break in machine direction of about 630% and in cross machine direction of about 765%. The percentages are average percentages of at least 5 samples. A person skilled in the art is using ASTM D882 can easily determine the elongation at break.

b. Thickness of the Material for the Rupturable Membranous Cap

The variation in the thickness of the rupturable membranous cap 16 can be measured by any suitable known means. For large regions, a caliper gauge may be suitable or method as disclosed in U.S. Pat. No. 6,231,556 issued to Osborn on May 15, 2001. For smaller regions, a more microscopic technique is required, for example embedding the rupturable membranous cap 16 in a setting resin, making thin cross section slices of this embedded rupturable membranous cap 16, and measuring the thickness or gauge of the rupturable membranous cap 16 in this cross section by use of, for example, a scanning electron microscope.

The film typically has an initial thickness that may be homogenous or varied prior to formation of the rupturable membranous cap 16 and is between about 1 and about 200 microns. The thickness may be from about 5 to about 100 microns, about 10 to about 75 microns, about 15 to about 50 microns or most typically from about 20 to about 40 microns. This film thickness is the caliper, measured as set out herein.

Variations in film thickness can be created by a multitude of techniques including embossing the film during manufacturing, applying a coat extrusion of varying thickness to a base film, creating a film from two or more substrates of different thickness, or joining together films. The variation of film thickness from one region to the next may be large or small. For example, the regions of varied thickness are typically less than about 5%, about 3%, about 1%, or even less than about 0.5% of the total surface of the rupturable membranous cap 16.

Film thickness may vary between the rupturable membranous cap 16 and the tampon holder tube 19. In some embodiments, the rupturable membranous cap 16 is thinner than the tampon holder tube 19. The film of the rupturable membranous cap may have breaches that have no thickness and single or multiple breaches. Breaches may include holes, perforations, slits, gaps, voids, openings, punctures, cracks, apertures, pores, etc.

c. Average Maximum Rupturable Membranous Cap Extension

The average maximum rupturable membranous cap 16 extension is a measure of how far the rupturable membranous cap 16 stretches before it ruptures. The moment of the maximum rupturable membranous cap 16 extension is observed by, as the tampon 14 is pushed through the tampon holder tube 19, camera and/or recorded video and is typically the moment of rupture of the rupturable membranous cap 16. The average maximum film extension is the distance measured from the highest point of the edge of the feminine hygiene product 50 to the rupture line, and it can be presented as a percentage of the total tampon 14 length. If the film ruptures along an uneven line, so that the rupturable membranous cap 16 thus has a non-uniform length at the moment of rupture then the average length of the rupturable membranous cap 16 at this moment is taken to equal the point, referred to above.

For example, for an arrangement with a tampon 14 which has a total length, from the flat bottom withdrawal end to the top of the rounded top portion of 6 cm, and an average maximum rupturable membranous cap 16 extension (average length of rupture line to edge of feminine hygiene product 50) of 2.0 cm, the percentage tampon 14 exposed as defined herein is (6 cm-2.0 cm)/6 cm×100%=66.6%. In one embodiment of the invention, the arrangement is such that it has at least 20% of the tampon 14 exposed beyond the point of average maximum rupturable membranous cap 16 extension. For purposes of the present invention, the average maximum rupturable membranous cap 16 extension can be readily determined by pushing the tampon from the feminine hygiene product 50 with a constant speed while recording the time of the start of the pushing of the tampon ($t_0$) and the time of the rupturable membranous cap 16 ruptures, which is observed as above ($t_r$; i.e., the first instance that the film forms a rupture), and then, the average point (length) of maximum rupturable membranous cap 16 extension/rupture can be calculated from the elapsed time $t_r$-$t_0$ and the known speed, and the percentage tampon 14 exposed can be calculated as above.

Typically this percentage is at least 30%, at least 40% or in certain embodiments herein, even at least 50%, or even at least 60%.

It is beneficial for a rupturable membranous cap 16 to be formed by stretching a stretchable plastic yieldable film that can be uniformly shaped and can provide a high percentage of tampons 14 exposed beyond maximum rupturable membranous cap 16 extension during tampon expulsion, which typically requires only a low expulsion force. Therefore, a typical embodiment of the invention is an arrangement that has a rupturable membranous cap 16 that is made from a stretchable plastic yieldable film that typically requires only a low expulsion force. Typically the resulting rupturable membranous cap 16 is less plastically extensible or stretchable than the film. The use of such a stretchable or plastic yieldable film, may allow for about 50%, about 60%, about 70%, or more than about 80% of the tampon 14 to be exposed at the maximum rupturable membranous cap 16 extension. These results may also be achieved by making a rupturable membranous cap 16 from a stretchable plastic yieldable film and subsequently submitting the formed rupturable membranous cap 16 to a step to reduce the stretchability, for example, a strain-hardening step to induce plastic yielding. In the case when the rupturable membranous cap 16 is strain neutral or strain hardening during extension/tampon travel, the force increases when the film is more extended, reaching the maximum force when the film ruptures.

d. Maximum Expulsion Force

The maximum expulsion force typically occurs at the moment the arrangement reaches the point of maximum rupturable membranous cap 16 extension. However this maximum expulsion force may occur prior to the rupture of the rupturable membranous cap 16, such as is the case if the rupturable membranous cap 16 is strain softening. The maximum expulsion force and the concurrent observation of the moment of rupture of the film may be determined by placing a arrangement of the invention in a device employing a Dillon Force Gauge (Mecmesin AFG50N) or similar gauge, which can measure the peak force or "maximum expulsion force." The measurement is done by following the procedures in the operating manual of the device concerning how to measure the peak force.

The force gauge is oriented such that a load cell 'foot' will travel in a horizontal direction, and it is mounted to a stand and it remains stationary during the test. A propelled, movable horizontal slider is affixed to the stand to one side of the force gauge and is controlled by a linear actuator. An anchored applicator clamp with an internal diameter set to correspond to a diameter of the feminine hygiene product 50 is attached to the slider. The clamp is used to hold the tampon holder tube 19 stationary during the test without deformation of the feminine hygiene product 50.

When using a telescoping tubes arrangement, the tampon holder tube 19 is anchored to the slider by the applicator clamp, the plunger 13 is still free to slide within the tampon holder tube 19. The slider and the force gauge are so aligned on the stand that the plunger's 13 longitudinal axis and the force gauge's load cell axis are in-line with each other, in this case a horizontal line. The non-expulsion end of the plunger 13 is positioned to face the load cell 'foot'.

When the slider is actuated, it will move the arrangement towards the load cell foot. The measurement is done at a constant speed setting of the device; a speed of 7.5 cm/sec is an exemplary speed for the test of the arrangements of the invention. When the slider engages the end of the plunger 13 against the load cell foot, the plunger 13 starts its travel within the tampon holder tube 19, first engaging the bottom of the tampon 14 and then expelling the tampon 14 through the rupturable membranous cap 16. All the while, the force gauge measures the expulsion force, as well as captures the peak expulsion force. The slider stops its movement towards the force gauge after expelling the tampon 14 from the tampon applicator 10 by the operator manually turning off the slider power source or using some other form of control that can turn off the power.

The device will give a reading for the maximum expulsion force. By coupling the device to a timer, the time of the start of the experiment defined for calculation purposes as the time the plunger 13 initially engages the bottom of the tampon 14, and the time of rupture are monitored, thereby, the extension of the rupturable membranous cap 16 at the moment of rupture can also be calculated. For the arrangements of the invention, the maximum expulsion force is typically below about 2500 grams-force, below about 2000 grams-force, below about 1500 grams-force, below about 1000 grams-force or even below about 700 grams-force. Generally, the arrangement has a maximum expulsion force from about 700 grams-force to about 2500 grams-force to rupture the rupturable membranous cap 16 and expel the tampon 14 through the rupturable membranous cap 16.

II. Regions of Rupture

Referring primarily to FIG. 3, the regions of rupture 18 separate a portion of the rupturable membranous cap 16 and a portion of the tampon holder tube 19. The regions of rupture 18 is adjacent to at least a portion of the tampon holder tube 19. When the regions of rupture 18 rupture, a portion of the rupturable membranous cap 16 separates from a portion of the tampon holder tube 19. The other portion of the rupturable membranous cap 16 which does not have any regions of rupture 18 remains connected to the second top portion 46 of the tampon holder tube 19 by the hinge 39.

It is desirable for the regions of rupture 18 to have a single rupture line, which does not entirely encircle the outer perimeter 20 of the rupturable membranous cap 16 or the tampon holder tube 19, but leaves a portion which does not have any regions of rupture 18. The region(s) which does not have regions of rupture 18 (i.e., the hinge 39) result in the rupturable membranous cap 16 remaining attached to the tampon holder tube 19.

The regions of rupture 18 may have changes in film thickness, thin lines, perforations, slits, or spots. They may be continuous ruptures, discontinuous ruptures, or a combination of both. FIG. 2 shows a feminine hygiene product 50 having regions of rupture 18 located between a portion of the bottom 38 of the rupturable membranous cap 16 and a portion of the first top portion 45 of tampon holder tube 19 in the form of discontinuous perforations.

The regions of rupture 18 may be any pattern including C-shaped, conical, diagonal, arched, parabolic, round, and semi-spherical. FIG. 1a shows the regions of rupture 18 pattern as an upside down u-shaped region. Referring to FIG. 7b, the pattern of the regions of rupture 18''' resemble an S shape. In another non-limiting example, the regions of rupture 18 can be zig-zagged, m-shaped, or any pattern which will rupture and allow the tampon 14 to expel.

The regions of rupture 18 width, length, and thickness may vary. The regions of rupture 18 may have thickness variations. FIG. 6 shows an applicator arrangement displaying the regions of rupture 18', 18" having varying degrees of thickness. FIG. 7a shows a partial view which includes an enlarged view of the regions of rupture 18', 18" showing the thickness variations and showing the thinness variations of the regions of rupture 18', 18'''.

III. Tampon Holder Tube

Referring primarily to FIG. 1a, the tampon holder tube 19 is preferably an elongate hollow tube that has a first end 17, a second end 23 opposite the first end 17, and a finger grip 12. Referring primarily to FIG. 2, the first end 17 includes a first top portion 45 and a second top portion 46. The first top portion 45 of the tampon holder tube is adjacent to the regions of rupture 18. The second top portion 46 is adjacent to the rupturable membranous cap 16, specifically the hinge 39.

Referring to FIG. 1a, the manufacturer of the feminine hygiene product 50 may vary the configuration of the tampon holder tube 19. The configuration of the tampon holder tube 19 is preferably created to anchor the rupturable membranous cap 16, specifically the hinge 39. The hinge 39 and the rupturable membranous cap 16 must be anchored so that the rupturable membranous cap 16 will not become detached during pre-insertion, insertion, or post-insertion of the tampon 14 into the vaginal cavity.

Referring to FIG. 3, it is further noted herein that the shape or configuration of the tampon holder tube 19 may vary as long as at least the hinge 39 of the rupturable membranous cap 16 remains connected to the tampon holder tube 19 during expulsion of the tampon 14. One of skill in the art will readily recognize obvious variants on those presented in the patent application herein. The tampon holder tube 19 can be of any suitable cross-sectional shape. Suitable cross-sectional shapes include, but are not limited to circular, oval, flattened circular, and elliptical. Preferably, the tampon holder tube 19 has a circular cross-sectional configuration.

The purpose of the applicator is to achieve side-to-side coverage of a tampon 14 within a female user's vaginal cavity. While not wishing to be bound by any particular theory, it is believed herein that side-to-side coverage is best achieved when the tampon 14, during expulsion, is directed by the unique design of the feminine hygiene products 50 shown.

The tampon holder tube 19 can be constructed from similar materials to other tampon holder tubes known in the art of the type used in tampon applicators currently in use. Examples of other such tampon holder tubes are disclosed in U.S. Pat. No. 5,346,468 issued to Campion, et al. on Sep. 13, 1994 and U.S. Pat. No. 5,558,631 issued to Campion, et al. on Sep. 24, 1996. In an alternative embodiment, the tampon holder tube 19 contains two layers. The first layer can be made of the same or different material than the second layer. The first layer is in contact with at least a portion of the second layer.

IV. Tampon

Referring to FIG. 5, generally, tampon 14 refers to any type of absorbent structure that is inserted into the vaginal canal or other body cavities for the absorption of fluid therefrom or for the delivery of active materials, such as medicaments or moisture. Generally, there are two types of tampons 14: 1) the self-sustaining tampon and 2) the fluid permeable bag tampon. Referring to FIG. 1a, a self-sustaining tampon 14 or a fluid permeable bag 14 may be stored within the tampon holder tube 19. Referring to FIG. 5, the first type of tampon 14 is the self-sustaining tampon. Tampons 14 are generally self-sustaining in that they will tend to retain its general shape and size before use. The tampon 14 has a withdrawal end 26 opposed to an insertion end 25. The insertion end 25 has a top portion 15. A tampon 14 may be straight or non-linear in shape, such as curved along the longitudinal axis. A typical self-sustaining tampon 14 is 40-60 mm long, the length measured from the tip of the top portion 15 to the withdrawal end 26 along the longitudinal axis. A typical compressed tampon is 10-16 mm wide corresponding to the largest cylindrical cross section, although the width may vary along the length.

The second type of tampon 14 is an easily deformable fluid permeable bag. The fluid permeable bag can also be an easily deformable fluid permeable bag consisting of absorbent chips, spheres, or fibers such that the fluid permeable bag is readily deformable with a force of less than 1 pound per square inch (hereinafter "psi"). The tampon is substantially deformable at pressures of less than 3 psi. The tampon 14 has an outer tampon perimeter 52, an insertion end 25, and a withdrawal end 26. The withdrawal end 26 of the fluid permeable bag has the trailing edge 29. In one preferred embodiment herein, the tampon 14 is a fluid permeable bag-like tampon. A withdrawal string 36 may be attached to the withdrawal end 26 of the tampon 14, as is conventional in the art.

When the fluid permeable bag tampon 14 is used with the present invention, the tampon 14 will spread 30% before expelling from the tampon holder tube 19.

The fluid permeable bag 14 is discussed in greater detail in co-pending patent application Ser. No. 001987654, filed May 18, 2003, entitled "Highly Deformable Tampon", to Osborn et al., V. Plunger Referring primarily to FIG. 2, the plunger 13 comprises a component that is used to expel a tampon 14 from its position within the tampon holder tube 19 when the plunger 13 is pushed manually into the tampon holder tube 19. The plunger 13 is usually pulled out to its operative position when the tampon holder tube 19 is placed in the vaginal cavity. Plunger 13 is then telescoped back into the tampon holder tube 19 towards the second end 23 thereof, pushing tampon 14 through the first end 17 expelling the tampon 14.

The plunger 13 can be any type of component that is suitable for this purpose. The plunger 13 can be constructed similarly to plungers of the type used in tampon applicators currently in use. An example of a suitable plunger is disclosed in U.S. Pat. No. 5,346,468 issued to Campion, et al. on Sep. 13, 1994 and U.S. Pat. No. 5,558,631 issued to Campion, et al. on Sep. 24, 1996.

It should also be understood that the plunger 13 is an optional component for use with the feminine hygiene product 50 and that the feminine hygiene product 50 will be fully functional if the plunger 13 is omitted, i.e., a user must insert and push the tampon 14 through the feminine hygiene product 50 digitally.

VI. Alternative Embodiments

As shown in FIG. 7c, projections 30 may be located on the rupturable membranous cap 16. The projections 30 may be located anywhere on the rupturable membranous cap 16. In one non-limiting example, as shown in FIG. 7c, while a projection 30 is located at the end of the rupturable membranous cap 16, the projections 30 may be located anywhere.

In a non-limiting example, the projections 30 are located on the interior at the bottom of the rupturable membranous cap 16. As the tampon 14 is expelled from the tampon holder tube 19, the projections 30 aide the tampon in being joined to the rupturable membranous cap 16. Because of the additional attachment by the projection(s) to ensure that the tampon is joined to the rupturable membranous cap during expulsion, the projection(s) ensure vaginal coverage. A plunger 13 may also expand the rupturable membranous cap 16. The projection 30 located at the base of the rupturable membranous cap 16 is especially useful for a conformable tampon 14 that expands during expulsion from the tampon holder tube 19.

In one non-limiting example, the rupturable membranous cap 16 and the tampon holder tube 19 may be one continuous film or sheet. In another non-limiting example, the rupturable membranous cap 16 and the tampon holder tube 19 may be the same film or sheet as the rupturable membranous cap 16.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A feminine hygiene product, comprising:
   a) a tampon comprising an outer tampon perimeter, a withdrawal end opposed to an insertion end, said insertion end comprising a top portion and
   b) a tampon applicator comprising a rupturable membranous cap permanently associated with a tampon holder tube,
   said tampon holder tube comprising a hollow interior portion, an interior surface, an exterior surface, an outer perimeter, a longitudinal axis, a first end dimensioned for insertion into the vaginal cavity, and a second end positioned oppositely to said first end,
   said tampon being housed in said tampon holder tube within said hollow interior portion of said tampon holder tube and substantially aligned with said longitudinal axis of said tampon holder tube in a pre-expelled position,
   said rupturable membranous cap covering at least a portion of said insertion end of said tampon, whereby during expulsion of said tampon from said tampon holder tube, said tampon contacts said rupturable membranous cap, thereby reorienting said tampon into a direction substantially non-aligned to said longitudinal axis of said tampon holder tube.

2. The feminine hygiene product according to claim 1 wherein said tampon comprises a fluid permeable bag and absorbent material loosely dispersed within said fluid permeable bag.

3. The feminine hygiene product according to claim 1 wherein said tampon rotates during expulsion from said tampon applicator.

4. The feminine hygiene product according to claim 1 wherein at least a portion of said tampon and at least a portion of said rupturable membranous cap rotate together during expulsion.

5. The feminine hygiene product according to claim 1 wherein said tampon applicator further comprises a plunger being slidably mounted in said hollow interior portion of said tampon holder tube, said plunger being adapted to expel said tampon through said first end of said tampon holder tube.

6. The feminine hygiene product according to claim 1 wherein before expulsion of said tampon, said rupturable membranous cap further comprises a region of rupture and the tampon holder tube further comprises a tampon holder tube region of rupture.

7. The feminine hygiene product according to claim 6 wherein said region of rupture on said rupturable membranous cap and said tampon holder tube region of rupture on said tampon holder tube are in contact with one another before expulsion of said tampon.

8. The feminine hygiene product according to claim 6 wherein said region of rupture on said rupturable membranous cap and said tampon holder tube region of rupture on said tampon holder tube have a configuration selected from a group consisting of C-shaped, conical, diagonal, arched, parabolic, round, and semi-spherical.

9. The feminine hygiene product according to claim 6 wherein said region of rupture on said rupturable membranous cap and said tampon holder tube region of rupture on said tampon holder tube comprise perforations.

* * * * *

UNITED STATES PATENT AND TRADEMARK OFFICE
CERTIFICATE OF CORRECTION

PATENT NO.         : 7,320,673 B2                                                Page 1 of 1
APPLICATION NO.    : 10/791976
DATED              : January 22, 2008
INVENTOR(S)        : Diana Lynne Gann et al.

It is certified that error appears in the above-identified patent and that said Letters Patent is hereby corrected as shown below:

Column 2
Line 57, after the word along, delete "a".

Column 6
Line 45, after the word rupture, delete "18',".
Line 46, delete "50'" ". Insert --50"--.

Signed and Sealed this

Nineteenth Day of August, 2008

JON W. DUDAS
*Director of the United States Patent and Trademark Office*